United States Patent [19]

Snyder et al.

[11] Patent Number: 5,389,363

[45] Date of Patent: Feb. 14, 1995

[54] COSMETIC COMPOSITIONS FOR LENGTHENING, COLORING AND CURLING EYELASHES

[75] Inventors: Florence Snyder, Sayreville; Gale Reinhart, Belford; Debbie DiGirolamo, Holmdel, all of N.J.

[73] Assignee: Revlon Consumer Products Corporation, New York, N.Y.

[21] Appl. No.: 52,346

[22] Filed: Apr. 23, 1993

[51] Int. Cl.$^6$ ............................................. A61K 7/032
[52] U.S. Cl. .................... 424/70.7; 424/63; 424/78.02; 424/401; 424/70.12; 514/938; 514/944
[58] Field of Search ............... 424/63, 70, 401, 78.02; 514/938, 944

[56] References Cited

U.S. PATENT DOCUMENTS

| | | | |
|---|---|---|---|
| 3,734,874 | 5/1973 | Kibler | 260/292 E |
| 4,233,196 | 11/1980 | Sublett | 260/292 N |
| 4,304,901 | 12/1981 | O'Neill | 528/290 |
| 4,335,103 | 6/1982 | Barker | 424/59 |
| 4,336,246 | 6/1982 | Leon-Pekarek | 424/63 |
| 4,791,140 | 12/1988 | Fukasawa | 514/845 |
| 4,871,536 | 10/1989 | Arraudeau | 424/59 |
| 4,950,475 | 8/1990 | Vishnupad | 424/83 |
| 4,973,473 | 11/1990 | Schneider | 424/63 |
| 4,980,155 | 12/1990 | Shah | 424/63 |
| 4,988,502 | 1/1991 | Ounanian | 424/63 |
| 5,013,543 | 5/1991 | Mercado | 424/63 |
| 5,039,518 | 8/1991 | Barone | 424/63 |
| 5,053,220 | 10/1991 | Arraudeau | 424/63 |
| 5,053,221 | 10/1991 | Robertson | 424/63 |
| 5,108,736 | 4/1992 | Schlossman | 424/63 |
| 5,118,496 | 6/1992 | Herstein | 424/63 |
| 5,154,916 | 10/1992 | Arraudeau | 424/63 |
| 5,158,762 | 10/1992 | Pierce | 424/47 |

OTHER PUBLICATIONS

Cyprus minerals Co., Material Safety datasheet –1991.
Kirk–Othmer Encyclopedia of Chemical Technology, vol. 18, p. 378, 1982.
CTFA Cosmetic Ingredient Handbook, 2nd Edition, 1988.
Ganex WP–660 Material Safety Data Sheet, Jan. 1992.
Lipo Chemicals Inc. –data sheet for LIPO PE BASE G–55, Sep. 1992.

Primary Examiner—Thurman K. Page
Assistant Examiner—Jyothsna Venkat
Attorney, Agent, or Firm—Julie Blackburn

[57] ABSTRACT

A cosmetic composition for lengthening, curling, and coloring human eyelashes comprising, by weight of the total composition:

10–25% of a gel composition comprising a film forming component that contains at least one water dissipatable polymer which is a polyester or a polyamide, and 75–90% of an oil in water emulsion base composition comprised of pigment, wax, and at least one oil soluble synthetic polymer, wherein when the gel composition is mixed into the base composition the water dissipatable polymer of the gel composition reacts with the oil soluble synthetic polymer of the base composition to provide a composition with superior lash lengthening properties.

19 Claims, No Drawings

COSMETIC COMPOSITIONS FOR LENGTHENING, COLORING AND CURLING EYELASHES

TECHNICAL FIELD

The invention is in the field of cosmetic compositions which are applied to human eyelashes.

BACKGROUND OF THE INVENTION

Mascara is one of the oldest known cosmetics. Since biblical times women have used it to lengthen and color their eyelashes. The earliest mascaras were pressed cakes containing soap and colored pigments. When a water wetted brush was touched to the cake, the moisture caused the mascara particles to cling to the bristles and produce a color payoff onto the lashes. Cake mascaras were popular for many years. However, the results achieved with cake mascaras often depended on the technique of the user and how much water was applied to the cake to make the emulsion.

In order to eliminate the inconsistency of cake mascaras, cream mascaras were developed. The water was added to the other mascara ingredients to provide a creamy emulsion which was packaged in a tube. A separate brush was sold with the tube. When the user wanted to apply mascara to the lashes, the tube was squeezed and the mascara ejected onto the brush. Cream mascara had the advantage of uniform consistency and texture, ease of application, and good drying qualities. But the tube container had definite disadvantages because the amount of mascara ejected from the container was difficult to control.

The invention of the "Mascaramatic" applicator revolutionized the mascara industry. The Mascaramatic applicator was similar to today's mascara containers except that the applicator was a grooved rod instead of a brush. These applicators also had a metering device that controlled the amount of mascara dispensed onto the applicator as it was withdrawn from the reservoir.

Today mascara is one of the most widely used cosmetics. In the traditional beauty regimen, the eyelashes are first curled with an eyelash curler. Mascara is then applied to color and lengthen the lashes. Curled eyelashes tend to "open" the eyes up and make them look bigger. The lengthening and coloring effect of the mascara on the eyelashes accentuates the eyes and enhances beauty. Many different types of mascaras in many colors are now available, and some are more popular than others. Since lash lengthening, thickening, and coloring is the effect to be achieved with mascaras, the formulations which perform these functions best tend to be most popular. Lash lengthening is a property which can always be improved. Moreover, most of the commercial mascara preparations do not provide a curling effect to the lashes.

An object of the invention is to provide a mascara formulation which provides superior lengthening and coloring effects to the lashes.

Another object of the invention is to provide a mascara formulation which causes the eyelashes to curl.

Another object of the invention is to provide a mascara composition which provides superior adherence to lashes, thus necessitating only one application.

SUMMARY OF THE INVENTION

The invention is directed to a cosmetic composition for lengthening, curling, and coloring human eyelashes comprising:
  10–25% of a gel composition comprising a film forming component that contains at least one water dissipatable polymer which is a polyester or a polyamide, and
  75–90% of an oil in water emulsion base composition comprised of pigment, wax, and at least one oil soluble synthetic polymer,
  wherein when the gel composition is mixed into the base composition the water dissipatable polymer of the gel composition reacts with the oil soluble synthetic polymer of the base composition to provide superior lash lengthening properties.

DETAILED DESCRIPTION

The mascara composition of the invention is a unique blend of a gel phase or gel composition and a oil in water emulsion base composition. When the gel phase is emulsified or mixed into the oil in water emulsion base the emulsion characteristics of the base are modified due to the presence of the gel. In particular, it is believed that the water dissipatable polymer in the gel composition reacts with the oil soluble synthetic polymer found in the base composition to provide a final composition with superior lash lengthening properties. The lash lengthening gives the impression of fibers without the problems of fibers.

The gel composition comprises, by total weight of the gel composition, about 35–65% silicone, and 1–40% of a film forming component which comprises, by weight of the film forming component, 1 to 4 parts of a water dissipatable polymer which is a polyester or polyamide, 1 to 4 parts humectant, and 2 to 6 parts water.

A wide variety of silicones may be suitable for use as the silicone component of the gel composition, including cyclic or linear volatile silicones, water insoluble nonvolatile silicones, higher viscosity silicones such as silicone gums, amino functional silicones, and the like.

The nonvolatile silicone may be either a polyalkyl siloxane, a polyaryl siloxane, a polyalkylaryl siloxane or a polyether siloxane copolymer. The term "nonvolatile" means polydimethylsiloxanes with viscosities ranging from about 5 to 600,000 centistokes at 25° C. These siloxanes are available from the General Electric Company as the Viscasil series and from Dow Corning as the Dow Corning 200 series. Preferably, the viscosity should range from 350 to 100,000 centistokes.

Silicone gums are also suitable for the gel phase. The term "silicone gum" generally denotes high molecular weight polydiorganosiloxanes having a mass molecular weight of at least 100,000 centistokes ranging up to 15 million centistokes. Specific examples include polydimethylsiloxane, methylphenyl-diphenyl siloxane copolymer, dimethiconol, polydimethylsiloxane/methylvinylsiloxane copolymer, (polydimethylsiloxane)(diphenyl)(methylvinylsiloxane) copolymer and mixtures thereof.

Volatile silicones are also suitable, and may be linear or cyclic volatile silicones. The cyclic silicone, cyclomethicone, is represented by the formula:

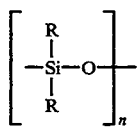

wherein R is a $C_1$–$C_3$ alkyl group or a phenyl group (preferably a methyl group) and n is a number from 3–10, preferably 3–7. Cyclomethicones are available as low viscosity fluids from a number of commercial sources such as General Electric, Dow Corning, and the like. These cyclic silicones are non-polar, insoluble in water, and completely miscible in lower alcohols, aliphatic aromatic solvents and halogenated hydrocarbon solvents. The volatile silicones may also be linear. Suitable linear silicones are also available from a number of commercial sources such as General Electric, Dow Corning, and the like.

Finally, amine functional silicones as set forth in U.S. Pat. No. 4,559,227, which is incorporated by reference, are also acceptable for use with the invention.

Preferably a mixture of volatile silicone and silicone gum is used. The silicone gum portion promotes adhesion of the composition to the lashes, and the volatile silicone component enhances the mascara dry time. A ratio of 50–99% volatile silicone and 1–50% silicone gum is suggested. The preferred embodiment of the invention contains a mixture of volatile silicone and silicone gum, in particular a 87:13 mixture of cyclomethicone and dimethiconol respectively.

The film forming component of the gel phase comprises, by weight of the total film forming component, 1 to 4 parts of a water dissipatable polymer which is a polyester or polyamide, 1 to 4 parts humectant, and 2 to 6 parts water. Film forming components of this composition are disclosed in U.S. Pat. No. 4,950,475 which is hereby incorporated by reference. The water dissipatable polymers which are suitable are set forth in U.S. Pat. Nos. 3,734,874, 4,233,196 and 4,304,901 which are also incorporated by reference. The preferred water dissipatable polymer is isophthalates/sulfoisophthalates copolymer.

For optimum effects it is suggested that the gel composition or phase also contain at least one synthetic polymer which is a powder at room temperature in a range of 1–50%, preferably 25–45% by weight of the gel phase. This synthetic polymer is generally not soluble in oil or water at room temperature. The term "powder" means a particulate, finely divided solid polymeric material having a particle size of 0.005 to 1000 microns. It is believed that the powder synthetic polymer reacts with the water dissipatable polymer of the gel phase and the oil soluble synthetic polymer of the oil in water emulsion base composition to produce fibers which enhance the lash lengthening properties of the mascara.

Preferred synthetic polymer powders falling into this category are $C_{2-20}$ polyalkylene copolymers such as polyethylene, acrylic/acrylate copolymer, nylon, acrylates copolymer, ammonium acrylates copolymer, ethylene/acrylate copolymer, ethylene/vinyl acetate copolymer, polychlorotrifluoroethylene, polytetrafluoroethylene, polyethylacrylate, styrene/acrylate/ammonium methacrylate copolymer, sodium $C_{4-10}$ olefin/maleic acid copolymer, or mixtures thereof.

The gel phase may also contain additional ingredients such as emollients, preservatives, and the like.

If emollients are present a range of 1–15% by weight of the total gel phase is suggested. Suitable emollients include N-alkoxyalkylamides set forth in U.S. Pat. No. 5,084,270 and fatty acid diesters set forth in U.S. Pat. Nos. 4,567,037, 4,639,369, and 4,867,965, all of which are incorporated by reference. Specifically, emollients such as methoxypropylgluconamide, glyceryl distearate, stearyl alcohol, cholesterol, $C_{12-15}$ alkyl benzoate, steareth-10, glyceryl monoricinoleate, glyceryl monostearate, propylene glycol, cetyl alcohol, hexyl laurate, decyl oleate, isopropyl myristate, isopropyl palmitate, myristyl alcohol, squalene, cocoa butter, propylene glycol/dicaprylate dicaprate, glyceryl monooleate, oleic acid, lanolin, acetylated lanolin alcohol, mineral oil, palmitic acid, diglycol stearate, avocado oil, sesame oil, octyl palmitate, and mixtures thereof. Preferred are a mixture of methoxypropylgluconamide, glyceryl distearate, stearyl alcohol, cholesterol, $C^{12-15}$ alkyl benzoate and steareth-10.

In the preferred embodiment of the invention the gel phase composition comprises, by total weight of the gel composition:
 about 40–60% silicone,
 about 3–10% emollient,
 about 5–20% of a film forming component comprising, by weight of the film forming component, 1 to 4 parts of a water dissipatable polymer which is a polyester or polyamide, 1 to 4 parts humectant, and 2 to 6 parts water; and
 about 30–40% of a synthetic polymer which is a powder at room temperature.

The second component of the mascara composition is an oil in water emulsion base composition. This base composition comprises, by total weight of the base composition, about 25–55% water, 1–30% pigment, 5–45% waxes, and 0.1–15% of an oil soluble synthetic polymer reactive with the water dissipatable polymer of the gel phase and with the powder synthetic polymer of the gel phase (if present).

Generally any iron oxide or ultramarine, chromiums, or manganese violet pigments may be used as the pigment phase, but most commonly iron oxide black or brown is used either alone or in combination with other colors such as violet, red, blue, or yellow.

Suitable waxes are defined as waxes having a melting point of 35° C. to 110° C. Waxes in this category include beeswax, paraffin, carnauba, ceresin, microcrystalline, ozokerite, acetylated lanolin, lanolin alcohol, cocoa butter, petrolatum, jojoba lanolin, shellac wax, spermaceti, bran wax, capok wax, montan wax, whale wax, or mixtures thereof. Preferred is a mixture of paraffin, beeswax, and carnauba wax.

The synthetic polymer of the base composition must be oil soluble and generally, but not always, has the consistency of a wax at room temperature. The term "consistency of wax" means that at room temperature the polymer is a solid or semi-solid pliable amorphous mass. Oil soluble polymers which fall into this category include oil soluble derivatives of polyvinylpyrrolidone (PVP), such as PVP/dimethylaminoethylmethacrylate copolymer, PVP/eicosene copolymer, PVP/ethyl methacrylate/methacrylic acid copolymer, PVP/hexadecene copolymer, PVP/VA copolymer, PVP/1-triacontene, and a polymer marketed under the tradename "Polyolprepolymer-2" by Barnet, Englewood Cliffs, N.J.

Preferred is PVP/1-triacontene or Tricontanyl PVP which has the CAS registry name 2-pyrrolidinone, 1-ethenyl-polymer with 1-triacontene with the synonym poly(vinyl pyrrolidone/1-triacontene). The triacontene moeity is a derivitive of triacontanoic or melissic acid which has the molecular formula $CH_3(CH_2)_{29}COOH$. This polymer is sold commercially under the tradename GanexWP-660 by ISP of Wayne N.J.

In addition, the base composition may contain other ingredients such as gums, emollients, preservatives, surfactants and so on.

Preferably the composition contains 0.1–15% by weight of the base composition of one or more gums. Gums are generally plant derived materials which have the unique ability to swell in the presence of water and increase viscosity. Suitable gums are acacia, agar, algin, alginic acid, ammonium alginate, calcium alginate, carrageenan, carboxymethyl hydroxyethyl cellulose, carboxymethyl hydroxypropyl guar, cellulose gum and/or derivatives thereof, dextran, dextrin, ethylcellulose, gelatin, guar gum, hydroxybutylmethylcellulose, hydroxypropylcellulose, maltodextrin, methylcellulose, xanthan, tragacanth or mixtures thereof.

Preservatives are also suggested in a range of 0.001–7% by weight of the base composition.

The base composition may also contain other emollients, and a range of 0.001–10% by weight of the base composition is suggested.

The preferred embodiment of the invention is a base composition comprising:
35–45% water,
0.5–10% gums,
5–20% pigment,
10–25% wax,
1–10% of an oil soluble synthetic polymer which is preferably a PVP derivative, most preferably Tricontanyl PVP.

In order to make the final mascara composition of the invention, the base composition is first made by mixing water, gums, pigments and surfactants, if present at a temperature of about 85° C. The oil phase ingredients are mixed separately at a temperature of about 85° C. Both mixtures are cooled to about 60° C. About 10–25 parts of gel phase is mixed with 75–90 parts of the oil in water emulsion phase to yield the composition of the invention.

The invention will be further described in connection with the following examples which are set forth for the purposes of illustration only.

EXAMPLE 1

The gel phase composition was made as follows:

| | | w/w % |
|---|---|---|
| 1. | cyclomethicone/dimethiconol (87:13) | 54.55 |
| 2. | methoxypropylgluconamide, glyceryl distearate, stearyl alcohol, cholesterol, $C_{12-15}$ alkyl benzoate, steareth - 10 | 6.06 |
| 3. | glycerin/diglycol/cyclohexanedimethanol/ isophthalates/sulfoisophthalates copolymer/water (40:30:30) | 6.30 |
| 4. | polyethylene | 34.30 |

Ingredients 1, 2, and 3 were slowly mixed. After mixing, ingredient 4 was added to make the final gel composition.

EXAMPLE 2

The final mascara composition was made as follows:

| | w/w % |
|---|---|
| Water | 44.70 |
| Hydroxyethylcellulose | 0.35 |
| Simethicone | 0.20 |
| Acacia | 1.25 |
| Diazolidinyl urea/methyl/propyl/paraben propylene glycol (20:10:10:60) | 1.00 |
| Iron oxide black | 0.50 |
| Silk powder | 0.50 |
| Chitin extract/water/propylene glycol (10:80:10) | 0.50 |
| Triethanolamine (99%) | 3.00 |
| Stearic acid | 7.40 |
| Paraffin | 10.00 |
| White beeswax | 3.00 |
| Carnauba | 3.00 |
| Glyceryl stearate | 2.50 |
| Tricontanyl PVP | 1.50 |
| Gel phase from Example 1 | 16.50 |

All of the ingredients except for the gel phase were emulsified together. After complete emulsification the gel phase was added and mixed into the composition.

EXAMPLE 3

Several mascara compositions were made as follows:

| | | w/w % | |
|---|---|---|---|
| | | 1 | 2 |
| 1 | Water | 39.00 | 39.00 |
| 1 | Acacia | 1.25 | 1.25 |
| 1 | Hydroxyethyl cellulose | 0.35 | 0.35 |
| 1 | Simethicone | 0.20 | 0.20 |
| 1 | Preservative | 1.00 | 1.00 |
| 1 | Black iron oxide | 10.00 | 10.00 |
| 2 | TEA | 3.00 | 3.00 |
| 2 | Water | 1.30 | 1.30 |
| 3 | Stearic acid | 7.40 | 7.40 |
| 3 | Paraffin | 10.00 | 10.00 |
| 3 | Beeswax | 3.00 | 3.00 |
| 3 | Carnauba | 3.00 | 3.00 |
| 3 | Glyceryl mono stearate | 2.50 | 2.50 |
| 3 | Tricontanyl PVP | 1.50 | 1.50 |
| 4 | Polyethylene | 5.00 | 5.00 |
| 4 | Cyclomethicone/ methiconol | 9.00 | 9.00 |
| 4 | Methoxypropyl gluconamide | 1.00 | 1.00 |
| 4 | Polymer 2 | 1.50 | — |
| 4 | glycerin/diglycol/ cyclohexanedi- methanol/iso- phthalates/ sulfoisophthalates copolymer/water (40:30:30) | — | 1.50 |

The #1 ingredients were mixed together and heated to 85° C. The #2 ingredients were then added and the heat increased to 85° C. The #3 ingredients were separately melted at 85° C. The #1, #2, and #3 phases are emulsified. The temperature of the #1, #2, and #3 mixtures was then reduced to 60° C. and the #4 ingredients were added. The final composition was cooled.

EXAMPLE 4

The mascara composition of Example 2 was tested on 18 panelists. The results are as follows:

Application/Appearance

Lengthening effect was rated as excellent/very good by all 18 panelists.

Deposit and thickening effect was rated excellent to good by all 18 panelists

Thick looking, non-clumping and overall appearance were rated well by 94% of the panel (17/18)

About 89% of the panelists (16/18) felt the test mascara curled well and was natural looking Lash separation was scored as excellent/very good by 83% of panelists (15/18)

Wear

About 94% of the panel (17/18) considered the mascara to be long wearing and left lashes pliant and silky when asked to compare the mascara to their current brand, 9 panelists felt the test mascara was better, 7 stated that it was comparable, and 2 considered it worse.

About 83% (15/18) of the group indicated a positive purchase intent

All 18 panelists reported that the test mascara removed well with soap and water The panelists were asked to apply the mascara and rate it for wear after 4 and 8 hours. They reported as follows:

|  | 4 hours | 8 hours |
|---|---|---|
| Overall wear (excellent to good) | 100% | 94% |

We claim:

1. A cosmetic composition for lengthening, curling, and coloring human eyelashes comprising, by weight of the total composition:
   10–25% of a gel composition comprising a film forming component that contains a water dissipatable polymer which is a polyester or polyamide, and
   75–90% of an oil in water emulsion base composition comprised of pigment, wax, and an oil soluble synthetic polymer selected from the group consisting of polyvinylpyrrolidone (PVP), PVP/dimethylaminoethylmethacrylate copolymer, PVP/eicosene copolymer, PVP/ethylmethacrylate/methacrylic acid copolymer, PVP/hexadecene copolymer, PVP/VA copolymer, PVP/1-triacontene, PPG-12 SMDI copolymer and mixtures thereof,
   wherein when the gel composition is mixed into the base composition the water dissipatable polymer of the gel composition reacts with the oil soluble synthetic polymer of the base composition to provide a composition with superior lash lengthening properties.

2. The composition of claim 1 wherein the gel composition comprises, by weight of the total gel composition, 35–65% silicone, and 1–40% of a film forming component comprising, by weight of the film forming component, 1 to 4 parts of a water dissipatable polymer which is a polyester or polyamide, 1 to 4 parts humectant, and 2 to 6 parts water.

3. The composition of claim 2 wherein the silicone is a cyclic or linear volatile silicone, a nonvolatile silicone, a silicone gum, an amine functional silicone, or mixtures thereof.

4. The composition of claim 3 wherein the gel phase additionally comprises 1–50% of a synthetic polymer which is a powder at room temperature.

5. The composition of claim 4 wherein the silicone comprises 50–99 parts volatile silicone and 1–50 parts silicone gum.

6. The composition of claim 5 wherein the silicone is a cyclomethicone/dimethiconol mixture.

7. The composition of claim 6 wherein the synthetic polymer powder is polyethylene, acrylic/acrylate copolymer, acrylates copolymer, ammonium acrylates copolymer, ethylene/acrylate copolymer, ethylene/vinyl acetate copolymer, polychlorotrifluoroethylene, polytetrafluoroethylene, polyethylacrylate, styrene/acrylate/ammonium methacrylate copolymer, sodium $C_{4-10}$ olefin/maleic acid copolymer, or mixtures thereof.

8. The composition of claim 7 wherein the water dissipatable polymer is isophthalates/sulfoisophthalates copolymer.

9. The composition of claim 8 wherein the synthetic polymer powder is polyethylene.

10. The composition of claim 9 comprising:
    about 40–60% silicone,
    about 3–10% emollient,
    about 5–20% of a film forming component comprising, by weight of the film forming component, 1 to 4 parts of a water dissipatable polymer which is a polyester or polyamide, 1 to 4 parts humectant, and 2 to 6 parts water,
    about 30–40% of a synthetic polymer which is a powder at room temperature.

11. The composition of claim 1 wherein the oil in water emulsion base composition comprises, by total weight of the base composition, about 25–55% water, 1–30% pigment, 5–45% waxes, and 0.1–15% of an oil soluble synthetic polymer reactive with the water dissipatable polymer of the gel composition.

12. The composition of claim 11 wherein the oil soluble synthetic polymer is Tricontanyl PVP.

13. The composition of claim 12 wherein the waxes are beeswax, paraffin, carnauba, ceresin, microcrystalline, ozokerite, acetylated lanolin, lanolin alcohol, cocoa butter, petrolatum, jojoba lanolin, shellac wax, spermaceti, bran wax, capok wax, montan wax, whale wax, or mixtures thereof.

14. The composition of claim 13 additionally comprising 0.1–15% by weight of the base composition of one or more gums.

15. The composition of claim 14 wherein the gums are acacia, agar, algin, alginic acid, ammonium alginate, calcium alginate, carrageenan, carboxymethyl hydroxyethyl cellulose, carboxymethyl hydroxypropyl guar, cellulose gum, dextran, dextrin, ethylcellulose, gelatin, guar gum, hydroxybutyl methylcellulose, hydroxypropyl cellulose, maltodextrin, methyl cellulose, xanthan, tragacanth and mixtures thereof.

16. The composition of claim 15 wherein the pigment is iron oxide.

17. The composition of claim 16 comprising:
    35–45% water,
    0.5–10% gums,
    5–20% pigment,
    10–25% wax,
    1–10% Tricontanyl PVP.

18. The composition of claim 17 additionally comprising 0.001–10% emollient.

19. A composition for lengthening, curling and coloring human eyelashes comprising:

10-25 parts of a gel composition comprising by weight of the gel composition, 40-60% silicone, 1-15% emollient, 30-40% of a synthetic polymer which is a powder at room temperature, 5-20% of a film forming component comprising, by weight of the film forming component, 1 to 4 parts of a water dissipatable polymer which is a polyester or polyamide, 1 to 4 parts humectant, and 2 to 6 parts water; and 75-90 parts of an oil in water emulsion base composition comprising by weight of the base composition 35-45% water, 0.5-10% gums, 5-20% pigment, 10-25% wax, and 1-10% Tricontanyl PVP, wherein when the gel composition is mixed into the base composition the water dissipatable polymer of the gel composition reacts with the Tricontanyl PVP and the synthetic powder polymer of the base composition to provide a composition with lash lengthening properties.

* * * * *